Figure 1:
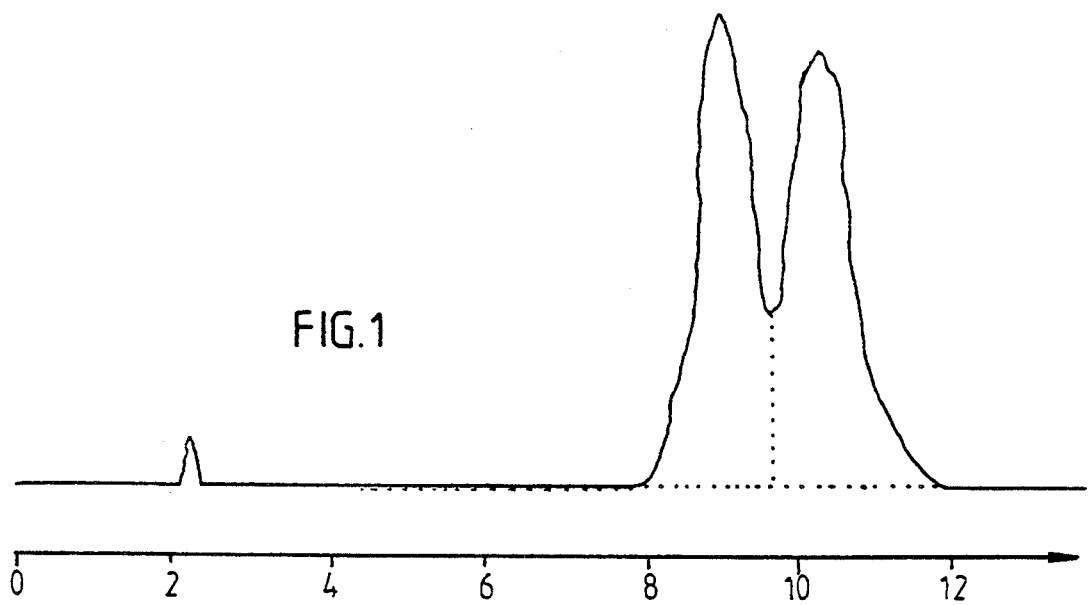

United States Patent [19]

Grosser et al.

[11] Patent Number: 5,354,884
[45] Date of Patent: Oct. 11, 1994

[54] OPTICALLY ACTIVE N-α-FLUOROACRYLOYLAMINO ACID DERIVATIVES FOR THE RESOLUTION OF RACEMATES

[75] Inventors: Rolf Grosser, Leverkusen; Walter Lange, Cologne; Bruno Bömer, Bergisch Gladbach; Dieter Arlt, Cologne; Dietmar Bielefeldt, Ratingen, all of Fed. Rep. of Germany

[73] Assignee: Bayer Aktiengesellschaft, Leverkusen, Fed. Rep. of Germany

[21] Appl. No.: 955,225

[22] Filed: Oct. 1, 1992

Related U.S. Application Data

[63] Continuation of Ser. No. 721,065, Jun. 26, 1991, abandoned.

[30] Foreign Application Priority Data

Jul. 3, 1990 [DE] Fed. Rep. of Germany ....... 4021108

[51] Int. Cl.$^5$ ............................................. C07C 229/30
[52] U.S. Cl. ........................................ 560/41; 560/39; 560/40; 560/43; 560/156
[58] Field of Search ................ 540/608; 546/225, 245; 548/530; 558/14, 254; 560/41, 39, 43, 40, 121, 122, 123, 124, 126, 128, 155, 170; 564/152, 155, 156, 160

[56] References Cited

U.S. PATENT DOCUMENTS 3,452,182 6/1969 Haas ..................................... 96/35.1
4,101,672 7/1978 Hubele et al. ........................ 558/14
4,474,692 10/1984 Oka et al. ............................. 560/41

FOREIGN PATENT DOCUMENTS 0282770 9/1988 European Pat. Off. .
0379917 8/1990 European Pat. Off. .
1570802 1/1970 Fed. Rep. of Germany .
2164692 7/1987 Japan .................................... 560/41
3270652 11/1988 Japan .................................... 560/41

OTHER PUBLICATIONS

Undheim, Chemical Abs. #72 (3) 11894g, 1969.
Chromatographic Science Series Bd. 40, 1988, New York; Basel; Seiten 179-198; Blaschke "Substituted Polyacrylamides as Chiral Phases for the Resolution of Drugs".

Primary Examiner—Nicholas S. Rizzo
Assistant Examiner—Yogendra N. Gupta
Attorney, Agent, or Firm—Sprung Horn Kramer & Woods

[57] ABSTRACT

α-Fluoro-substituted N-acryloylamino acid derivatives of the formula

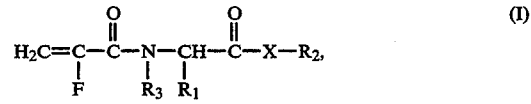

are used to make polymers optionally for chromatographic resolution of racemates into their enantiomers. The fluorine atom improves performance in many instances.

5 Claims, 4 Drawing Sheets

OPTICALLY ACTIVE N-α-FLUOROACRYLOYLAMINO ACID DERIVATIVES FOR THE RESOLUTION OF RACEMATES

This application is a continuation of application Ser. No. 721,065, filed Jun. 26, 1991 now abandoned.

The invention relates to novel optically active N-α-fluoroacryloylamino acid derivatives, to a process for their preparation, to their polymerization to give optically active polymers and to the use of these optically active polymers as adsorbents for the chromatographic resolution of racemates into their enantiomers.

In recent years, the resolution of racemates of active compounds has become increasingly important, since it has been shown that the enantiomers of the racemate of an active compound often differ in their biological effects and side effects.

Apart from the classic methods for the resolution of racemates, chromatographic resolution of racemates has proved particularly suitable in recent times. Apart from natural product derivatives, for example based on cellulose, synthetic optically active poly(meth)acrylamides have increasingly been used as adsorbents (Review: G. Blaschke, Chromatogr. Sci. 1988, 40, 179-198).

However, when applying the known methods, it was found that they either have an inadequate effect or only have an efficiency which is limited to certain racemates.

Surprisingly, it has now been found that polymers made of optically active α-fluoroacrylamides of amino acid esters or amino acid amides are adsorbents with very good racemate-resolving properties.

Surprisingly, the substitution of the hydrogen atom or the methyl group in the (meth)acrylamides by the strongly electronegative fluorine atom does not lead to a loss in separation efficiency, as would be expected owing to the opposite electronic effect and the vicinity of the fluorine atom to the amide group, which, as is known, has to interact with the enantiomers of the racemate to be resolved via hydrogen bridges.

Rather, it is observed that racemates which pass through the corresponding poly(meth)acrylamide adsorbent unresolved can in many cases be resolved into enantiomers by the novel polyfluoroacrylamides of this type.

Thus, the polyfluoroacrylic acid derivatives according to the invention unexpectedly give rise to adsorbents for the chromatographic resolution of racemates, whose properties differ significantly from those of the corresponding (meth)acrylamides.

The invention relates to N-60 -fluoroacryloylamino acid derivatives of the formula (I)

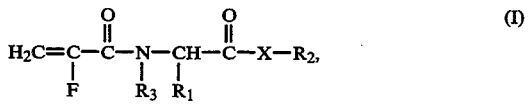

in which $R_1$ represents a straight-chain or branched $C_1-C_8$-alkyl, a $C_7-C_{12}$-aralkyl, a $C_3-C_{10}$-cycloalkyl, a $C_6-C_{14}$-aryl or a furyl, thienyl or pyridyl radical, which are unsubstituted or substituted by benzyloxycarbonyl, alkoxycarbonyl of up to 6 C atoms, hydroxyl, alkyl, cycloalkyl or alkoxy each having up to 6 C atoms, halogen, phenoxy, benzoxy, acylamino of up to 8 C atoms or by carbonylalkoxy of up to 6 C atoms, $R_3$ represents hydrogen or $C_1-C_4$-alkyl or together with $R_1$ forms a tri- or tetramethylene group, X is oxygen or an $NR_4$ group, in which $R_4$ represents hydrogen or straight-chain or branched $C_1-C_4$-alkyl or together with $R_2$ and the nitrogen atom forms a 5- to 7-membered ring which is unsubstituted or substituted by an alkoxycarbonyl group of up to 6 carbon atoms or by one or two alkyl groups each having 1 to 4 carbon atoms, $R_2$ represents a straight-chain or branched $C_1-C_{22}$-alkyl, $C_7-C_{12}$-aralkyl, $C_3-C_{10}$-cycloalkyl, $C_6-C_{14}$-aryl or a terpenyl radical, each of which is unsubstituted or substituted by halogen, alkyl or alkoxy each having 1 to 4 C atoms, or $R_1$ together with the group $X-R_2$ represents the radical

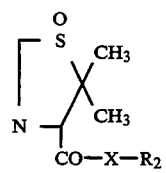

Examples of suitable substituted or unsubstituted straight-chain or branched $C_1-C_8$-alkyl as radicals $R_1$ are methyl, ethyl, i-propyl, n-propyl, n-butyl, i-butyl, t-butyl, 1-hydroxymethyl, 1-hydroxyethyl, 3-acetylaminopropyl, 4-benzoylaminobutyl, t-butoxymethyl, benzyloxymethyl, 2-methoxycarbonylmethyl, 3-methoxycarbonylethyl, 4-t-butoxycarbonylpropyl or, for example, 2-cyclohexylethyl; examples of substituted or unsubstituted $C_7-C_{12}$-aralkyl are benzyl, 1-naphthylmethyl, 2-naphthylmethyl, 3-indolylmethyl, 4-hydroxybenzyl, 2-phenylbutyl, 3-phenylbutyl and 4-phenylbutyl; examples of substituted or unsubstituted straight-chain or branched $C_4-C_{10}$-cycloalkyl are cyclopropyl, cyclobutyl, cyclopentyl, cyclohexyl or decahydronaphthyl; examples of substituted or unsubstituted $C_6-C_{14}$-aryl are phenyl, 1-naphthyl and 2-naphthyl.

Examples of radicals $R_4$ are hydrogen, methyl, ethyl, n-propyl, i-propyl, n-butyl and i-butyl, while examples of a substituted or unsubstituted ring are pyrrolidinyl, piperidinyl, morpholinyl, 2-alkoxycarbonylpyrrolidinyl and 2-alkoxymethylpyrrolidinyl each having 1 to 4 C atoms in the alkoxy group.

Examples of radicals $R_2$ are unsubstituted or halogen- or alkoxy-($C_1-C_4$)-substituted straight-chain or branched $C_1-C_{22}$-alkyl radicals, such as methyl, ethyl, trifluoroethyl, 2-chloroethyl, n-propyl, i-propyl, hexafluoroisopropyl, 2-methoxyethyl, 2-t-butoxyethyl, n-butyl, i-butyl, t-butyl, 2-octyl, 2-nonyl, stearyl and behenyl; substituted or unsubstituted $C_7-C_{12}$-aralkyl radicals, such as benzyl, 1-phenylethyl and 1-naphthylethyl; unsubstituted or halogen-, alkoxy-($C_1-C_4$)- or alkyl-($C_1-C_4$)-substituted $C_4-C_{10}$-cycloalkyl radicals, such as cyclobutyl, cyclopentyl, cyclohexyl, 2,6-dimethylcyclohexyl, 3,5-dimethylcyclohexyl, 4-t-butylcyclohexyl or decahydronaphthyl; unsubstituted or halogen-, alkoxy-($C_1-C_4$)- or alkyl-($C_1-C_4$)-substituted $C_6-C_{14}$-aryl radicals, such as phenyl and 1-naphthyl and 2-naphthyl; furthermore racemic or advantageously optically active terpenyl radicals, such as menthyl, 8-phenylmenthyl, neomenthyl, isomenthyl, bornyl, fenchyl, pinanyl and isopinocamphyl. Chiral radicals $R_2$ can be used in racemic form or advantageously in optically active form.

Compounds of the general formula (I) in which $R_1$ represents alkyl of 1 to 4 C atoms, benzyl, cycloalkyl of 3 to 7 C atoms, phenyl, indolylmethyl, naphthyl, naphthylmethyl, furyl, thienyl or pyridyl, in which the alkyl and aryl radicals mentioned are unsubstituted or mono- or disubstituted by hydroxyl, methoxy, halogen, alkyl, cycloalkyl of up to 6 C atoms, phenoxy, benzoxy, acetylamino, benzyloxycarbonyl or alkoxycarbonyl of up to 4 C atoms, $R_3$ represents hydrogen, methyl or ethyl or together with $R_1$ forms a tri- or tetramethylene group, X represents oxygen or an $NR_4$ group, in which
$R_4$ represents hydrogen or alkyl of 1 to 4 C atoms or together with $R_2$ and the nitrogen atom forms a 5- to 7-membered ring which is unsubstituted or substituted by alkyl or alkoxycarbonyl each having up to 4 C atoms, and $R_2$ represents alkyl of up to 12 C atoms, benzyl, cycloalkyl of 3 to 7 C atoms, phenyl or terpenyl, in which the radicals mentioned are unsubstituted or substituted by fluorine, chlorine or bromine or by alkyl or alkoxy each having up to 2 C atoms, or $R_1$ together with the group X-$R_2$ represents the radical

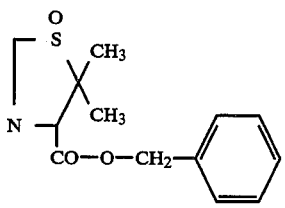

are of particular interest.

The optically active N-α-fluoroacryloylamino acid derivatives, according to the invention, of the formula (I) are preferably derived from optically active amino acids, such as alanine, aminobutyric acid, valine, norvaline, leucine, isoleucine, terleucine, phenylglycine, naphthylglycine, phenylalanine, thienylalanine, pyridylalanine, naphthylalanine, cyclohexylglycine, cyclohexylalanine, tyrosine, tryptophan, serine, aspartic acid, glutamic acid, ornithine, lysine, proline or 6-aminopenicillanic acid, i.e. $R^1$ preferably represents alkyl of 1 to 4 C atoms, benzyl, cyclohexyl, phenyl, indolylmethyl, naphthyl, naphthylmethyl, thienyl or pyridyl, in which the alkyl and aryl radicals mentioned may be unsubstituted or monosubstituted by hydroxyl, phenoxy, benzoxy, acetylamino, benzyloxycarbonyl or alkoxycarbonyl of up to 4 C atoms, or $R_1$ together with $R_3$ forms a trimethylene group which is substituted by $C_1$-$C_4$-alkoxycarbonyl or
$R_1$ together with X-$R_2$ forms the radical

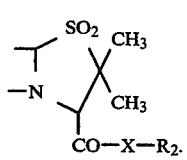

The optically active N-fluoroacryloylamino acid derivatives, according to the invention, of the formula (I) are obtained either A) by reaction of optically active amino acid derivatives of the formula

in which
$R_1$, $R_2$ and $R_3$ are as defined under formula (I), or their acid addition products, with fluoroacryloyl derivatives of the formula

in which
Y represents fluorine, chlorine or bromine, if appropriate in the presence of an acid-binding agent in inert organic solvents,
or
B) by reaction of compounds of the formula (II) with a fluorine compound of the formula

in which
Y is as defined above, and
A and Z each represent hydrogen, fluorine, chlorine or bromine, in which A and Z never simultaneously denote hydrogen, thus enabling the fluoroacryloyl compound (III) to be liberated by elimination of AZ, in which AZ is preferably HF, HCl, HBr, $Br_2$ or $Cl_2$.

α-Fluoroacryloyl derivatives of the formula (III) or precursors thereof (IV) can be prepared by processes known per se [Zh. Org. Khim. 28, 1173 (1987)] and can, if desired, also be used in the form of acid anhydrides.

The optically active amino acid esters of the formula (II) used as starting compounds are known or can be prepared by processes known per se (see Bull. Chem. Soc. Jap. 37 (1964), 191).

Suitable acid addition compounds of the amino acids to be used as starting compounds are salts of these amino acids with inorganic or organic acids. Mineral acids, such as hydrochloric acid, hydrobromic acid, sulphuric acid, phosphoric acid or organic acids, such as acetic acid, methane-, ethane-, benzene- or toluene-sulphonic acid, are preferred.

Suitable solvents are all organic solvents which are inert under the reaction conditions. Hydrocarbons, such as benzene, toluene, xylene, or petroleum fractions, or halogenated hydrocarbons, such as di-, tri- or tetra-chloromethane, dichloroethane or trichloroethylene, or ethers, such as tert.-butyl methyl ether or tert.-amyl ethyl ether are preferred.

Suitable acid-binding agents are in particular the customary inorganic or organic bases; alkali metal hydroxides or alkaline earth metal hydroxides, such as sodium hydroxide, potassium hydroxide, lithium hydroxide, calcium hydroxide or barium hydroxide, alkali metal carbonates or alkaline earth metal carbonates, such as sodium carbonate or potassium carbonate or sodium bicarbonate, alkali metal alcoholares, such as sodium methoxide, sodium ethoxide, potassium methoxide, potassium ethoxide, potassium t-butoxide, or amines, such as triethylamine or pyridine, are preferably used.

The reaction of the α-fluoroacryloyl derivatives of the formula (III) with the amino acid derivatives of the formula (II) is preferably carried out at temperatures of −78° to +100° C., in particular −20° C. to +60° C.

The invention also relates to the optically active polymers and copolymers obtainable by polymerization or copolymerization of the optically active N-α-fluoroacryloylamino acid derivatives of the formula (I) and containing at least 40 mol %, preferably at least 50 mol %, of structural units of the formula (V)

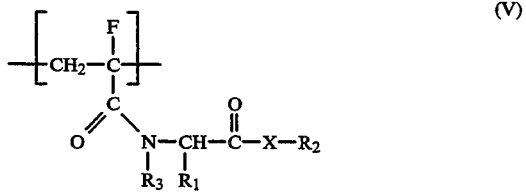

in which $R_1$, $R_2$, $R_3$ and X are as defined under formula (I).

The optically active polymers, according to the invention, of the formula (V) are preferably present in the form of crosslinked insoluble or swellable bead polymers or in a form in which they are bound to finely divided inorganic support materials such as, for example, silica gel. They can also be prepared as linear polymers soluble in suitable organic solvents. It is furthermore possible to copolymerize different N-α-fluoroacryloylamino acid derivatives, according to the invention, of the formula (I) and to incorporate 0.1 to 60, preferably 0.1 to 20, mol % of copolymerizable other monomers in the polymers.

The crosslinked polymers are preferably present in the form of small particles (beads) having a particle diameter of 5 to 200 μm. They are prepared, for example, by suspension polymerization of the optically active N-α-fluoroacryloylamino acid derivatives of the formula (I) with 0.5 to 50 mol %, preferably 1 to 30 mol %, particularly preferably 3 to 20 mol %, (relative to the total amount [mol] of the monomers used), of a suitable crosslinking agent in a manner known per se.

The degree of swelling of the (bead) polymers can be adjusted by conventional methods via the type and amount of the crosslinking agents.

In practical use, (bead) polymers having a degree of swelling (Q) of 1.1 to 10, preferably 2.0 to 7.0, have proved suitable.

The degree of swelling Q is determined as follows:

$$Q = \frac{\text{polymer volume (swollen)}}{\text{polymer volume (unswollen)}}$$

Suitable crosslinking agents are compounds containing at least two polymerizable vinyl groups. Preferred crosslinking agents are alkanediol diacrylates, such as 1,6-hexanediol diacrylate, 1,4-butanediol diacrylate, 1,3-propanediol diacrylate or 1,2-ethylene glycol diacrylate, or alkanediol methacrylates, such as 1,4-butanediol dimethacrylate, 1,3-butanediol dimethacrylate, 2,3-butanediol dimethacrylate, 1,3-propanediol dimethacrylate or 1,2-ethylene glycol dimethacrylate, aromatic divinyl compounds, such as, for example, divinylbenzene, divinylchlorobenzene or divinyltoluene, vinyl dicarboxylates, such as divinyl adipate, divinyl benzene dicarboxylate, divinyl terephthalate, N,N'-alkylenediacrylamides, such as N,N'-methylenediacrylamide, N,N'-ethylenediacrylamide, N,N'-methylenedimethacrylamide or N,N'-ethylenedimethacrylamide.

Suitable free-radical formers are the conventional free-radical formers. Peroxides, such as, for example, dibenzoyl peroxide, dilauroyl peroxide or di-ortho-tolyl peroxide, or azo compounds, such as, for example, azobisisobutyronitrile (AIBN) are preferred. Mixtures of various free-radical formers can also be used.

The polymerization components are dissolved in an organic solvent which is not miscible with water, preferably an aliphatic or aromatic hydrocarbon, such as hexane, heptane, isododecane, benzene or toluene, a halogenated hydrocarbon, such as di-, tri-, tetrachloromethane or 1,2-dichloroethane or an ester, such as ethyl acetate or butyl acetate.

The organic phase is evenly distributed in the aqueous solution of a protective colloid, preferably in an aqueous solution of polyvinyl alcohol, polyvinylpyrrolidone or a copolymer consisting of methacrylic acid and methyl methacrylate, by means of an efficient stirrer. About 1 to 20, preferably 2 to 10, parts by weight of aqueous phase are used per part by weight of organic phase. The polymerization mixture is heated in an inert gas atmosphere, preferably under nitrogen, to temperatures of 30° C. to 150° C., preferably 40° C. to 80° C., with stirring. The polymerization time is 2 to 24, preferably 4 to 12, hours. The copolymer obtained in this manner is separated from the liquid phase by filtration, purified by thorough washing with water and with organic solvents, such as methanol, ethanol, benzene, toluene, di- or trichloromethane or acetone, and then dried.

In particular for analytical applications, the optically active polymers according to the invention are preferably used in a form in which they are bound to finely divided inorganic supports. The preparation of optically active chromatographic phases of this type can be carried out, for example, by the processes described in DE-A-3,706,890.

Preference is given to the polymerization of the optically active N-α-fluoroacryloylamino acid derivatives of the formula (I) in the presence of vinyl/silica gels or silical gel/diol phases esterified with (meth)acrylic acid. This polymerization can be carried out in the absence of solvents or in the presence of solvents or precipitants for poly-N-α-fluoroacrylamides. The free-radical formers used for the preparation of the bead polymers can also be used as initiators.

The polymer-modified silica gels preferably contain 1 to 40% by weight, in particular 5 to 30% by weight, of optically active polymer (V), relative to the total weight. They are thoroughly washed with solvents for the polymer and dried in vacuo.

It is of course also possible here to use mixtures of two or more of the N-α-fluoroacryloylamino acid derivatives according to the invention, if appropriate also together with further copolymerizable monomers.

The invention furthermore relates to the use of the poly-N-α-fluoroacrylamides, according to the invention, of the formula (V) as such or in crosslinked or silica gel-bound form for the chromatographic resolution of racemic mixtures into the optical antipodes.

Examples of readily resolvable racemates are oxazepam, binaphthol, benzoin, chlorothalidone, thalidomide, N-3,5-dinitrobenzoylleucine, 1-(9-anthryl)2,2,2-trifluoroethanol and tetrahydro- and hexahydrocarbazole derivatives, such as, for example, 3-(4-chlorophenylsulphonamido)-9-(2-carboxyethyl),1,2,3,4-tetrahydrocarbazole, 3-r-(benzene-sulphonamido)-9-(2-carboxyethyl)-1,2,3,4,4a,9a-hexahydrocarbazole, 1-(carboxymethyl)-6-fluoro-9-(4-chlorobenzyl)-1,2,3,4-tetrahydrocarbazole, hydroxyalkylazole derivatives, such as, for example, 2-(4-chlorophenyl)-3-methoxyimino-3-methyl-l-(1,2,4-triazol-1-yl)-2-butanol and α-(4-fluorophenyl)-α-(1-cyanocyclopropyl)-1H-(1,2,4-triazol-1-yl)-ethanol and 1,4-dihydropyridine derivatives, such as, for example, 5-monoethyl 1,4-dihydro-2,6-dimethyl-4-(2-trifluoromethylphenyl)-3,5-dicarboxylate.

The composition of the eluent can be selected in the usual manner and optimized, depending on the type and the property of the racemate to be resolved. The poly-N-α-fluoroacryloylamino acid derivatives according to the invention which are bound to silica gel can be used for resolutions of racemates under HPLC conditions.

The capacity of the polymers for the resolution of racemates is expressed in terms of the capacity ratios ($k'_{1(2)}$ values) for the two enantiomers (1) and (2) and the resulting enantioselectivity value α. These chromatographic parameters are defined as follows:

$$\text{Capacity ratio } k_{1(2)} = \frac{t_{1(2)} - t_o}{t_o}$$

$$\text{Enantioselectivity } \alpha = \frac{k'_2}{k'_1}$$

$t_o$ = dead time of the column
$t_{1(2)}$ = retention time of the first eluted enantiomer 1 or of the later eluted enantiomer 2

The preparative resolution of racemic mixtures into their optical antipodes using the polymers according to the invention is preferably carried out by column chromatography. This is particularly advantageously done by carrying out the chromatographic separation using bead polymers of a definite particle size distribution; good separation efficiencies are obtained with bead polymers of a particle size distribution of 5 to 200 μm, preferably 15 to 100 μm.

The operating procedure of separation by column chromatography is known. Usually, the polymer is suspended in the eluent, and the suspension is poured into a glass column. After the eluent has been drained, the racemate to be resolved is applied to the column as a solution in the minimal amount of eluent. It is then eluted using the eluent, and the enantiomers in the eluate are detected by photometry and/or polarimetry by means of suitable flow cells.

The eluents used are conventional organic solvents or solvent mixtures which swell the polymer used as the adsorbent and dissolve the racemate to be resolved. Examples are: hydrocarbons, such as benzene, toluene or xylene, ethers, such as diethyl ether, t-butyl methyl eter, dioxane or tetrahydrofuran, halogenated hydrocarbons, such as di- or trichloromethane, acetone, acetonitrile or ethyl acetate, alcohols, such as methanol, ethanol, n-propanol, isopropanol or n-butanol, or else mixtures of the solvents mentioned. Mixtures of toluene with tetrahydrofuran, dioxane or isopropanol have proved particularly suitable.

The invention will be further described hereinbelow with reference to the accompanying drawings wherein
FIGS. 1 to 9 are chromatograms showing elution times in minutes on the horizontal axis and concentration of active material in the eluate vertically, for different racemates and adsorbents in accordance with the present invention.

EXAMPLES

I. Preparation method of N-α-fluoroacryloylamino acid derivatives (monomers)

Method a) starting from 2,3-difluoropropionyl chloride

A solution of 0.2 mol of 2,3-difluoropropionyl chloride in 200 ml of anhydrous dichloromethane is initially introduced, 0.205 mol of triethylamine is added dropwise at 0° C., and the mixture is stirred at 0° C. for 30 minutes.

A mixture of 0.2 mol of the amino acid derivative and 0.2 mol of triethylamine in 200 ml of anhydrous dichloromethane is then added dropwise to this solution at −10° C.

The mixture is allowed to reach room temperature and then subjected to aqueous work up as usual.

Method b) using α-fluoroacryloyl chloride

First 0.2 mol of triethylamine is added dropwise at 0° C. to a solution of 0.1 mol of an amino acid ester or amide hydrochloride of the formula (II) in 300 ml of dichloromethane, followed by dropwise addition of a solution of 0.1 mol of α-fluoroacryloyl chloride in 25 ml of dichloromethane at −10° C. The mixture is stirred for 30 minutes without cooling, washed in succession with water, 1N HCl and saturated NaHCO₃ solution, dried over magnesium sulphate and freed from the solvent on a rotary evaporator. The product obtained after drying in a high vacuum is recrystallized or purified by chromatography on silica gel.

If a free amino acid ester or amide is used, the amount of triethylamine is reduced to half. The N-α-fluoroacryloylamino acid derivatives thus prepared are listed in Table I.

TABLE I

| | Optically active monomers (I) | | | | |
|---|---|---|---|---|---|
| Example No. | N-α-fluoroacryloylamino acid derivative | Preparation method | M.p. (°C.) | Angle of rotation (c = 1, CHCl₃) | Yield (% of theory) |
| 1 | N-fluoroacryloyl-L-phenylalanine ethyl ester | a | 36° C. | +112° | 65 |
| 2 | N-fluoroacryloyl-L-phenylalanine n-propyl ester | a | 31° C. | +103° | 73 |
| 3 | N-fluoroacryloyl-L-phenylalanine i-propyl ester | a | 82° C. | +106.9° | 78 |
| 4 | N-fluoroacryloyl-L-phenylalanine t-butyl ester | b | 71° C. | +103.2° | 89 |

TABLE I-continued

| | | Optically active monomers (I) | | | |
|---|---|---|---|---|---|
| Example No. | N-α-fluoroacryloylamino acid derivative | Preparation method | M.p. (°C.) | Angle of rotation (c = 1, CHCl$_3$) | Yield (% of theory) |
| 5 | N-fluoroacryloyl-L-phenylalanine d-menthyl ester | b | oil | +85.4° | 63 |
| 6 | N-fluoroacryloyl-L-alanine d-menthyl ester | b | 34° C. | +55.8° | 83 |
| 7 | N-fluoroacryloyl-L-alanine l-bornyl ester | b | 80° C. | −38.1° | 80 |
| 8 | N-fluoroacryloyl-L-alanine (+)-fenchyl ester | b | oil | +36.4° | 83 |
| 9 | N-fluoroacryloyl-L-leucine t-butyl ester | b | 47° C. | +3.1° | 83 |
| 10 | N-fluroacryloyl-D-phenylglycine t-butyl ester | b | 117° C. | −176.8° | 64 |

II. Polymerization of the N-α-fluoroacryloylamino acid derivatives (I)

1. Preparation in the silica gel-bound form a) 25 g of silica gel modified with 1,2-diol groups (average particle size: 5 μm) are suspended in 500 ml of dioxane with the exclusion of moisture and under nitrogen. 16 ml of methacrylic anhydride and 12.5 ml of triethylamine are added to the suspension. The mixture is stirred at room temperature for 1 hour and stored at room temperature for 24 hours. The silica gel is then filtered off with suction through a sintered glass crucible (G4), stirred 3 times with 500 ml each of dioxane for 30 minutes, and sucked thoroughly dry in between. The silica gel modified with methacryloyl groups is dried at room temperature in a vacuum at <0.005 atm.

Yield 24.8 g Elemental analysis: C: 9.2%; H: 1.7%

Values of the silica gel modified with diol groups: C: 7.7%; H: 1.5% b) 3 g of the silica gel modified with methacryloyl groups, the preparation of which is described under a), 6.0 g of optically active N-α-fluoroacryloylamino acid derivative and 60 mg of azobisisobutyronitrile are dissolved or suspended in 25 ml of dry toluene in a 100 ml round-bottom flask equipped with reflux condenser and magnetic stirrer. The apparatus is freed from air by evacuating it and filling it with nitrogen three times, and then filled with nitrogen. The polymerization mixture is stirred at room temperature for 1 hour and then rapidly heated to 80° C. After stirring at 80° C. for 45 minutes, 200 mg of 2,6-di-tert.-butyl-4-methylphenol are added, and the reaction mixture is rapidly cooled. The silica gel is filtered off with suction through a sintered glass crucible (G4), washed with toluene and stirred twice with 50 ml each of chloroform, once with 50 ml of toluene and once with 50 ml of isopropanol for 30 minutes each and filtered off with suction in between. The silica gel is finally dried at room temperature in vacuo at <0,005 atm. In Table II below, the N-α-fluoroacryloylamino acid derivatives polymerized onto the modified silica gel, the yields of silica gel containing optically active compounds, its nitrogen content and its bound polymer content are summarized.

c) In the apparatus described under b), 3.0 g of the silica gel modified with methacryloyl groups, the preparation of which is described under a), 6.0 g of optically active N-α-fluoroacryloylamino acid derivative and 60 mg of azobisisobutyronitrile are dissolved or suspended in 25 ml of dry trichloromethane. The apparatus is freed from air by alternate evacuation and filling with nitrogen three times, and finally filled with nitrogen. The reaction mixture is stirred at room temperature for 1 hour and under reflux for 1 hour. After addition of 200 mg of 2,6-di-tert.-butyl-4-methylphenol, the batch is rapidly cooled. The silica gel is filtered off with suction through a sintered glass crucible (G4), stirred twice with 50 ml each of chloroform, once with 50 ml of toluene and once with 50 ml of isopropanol for 30 minutes each and filtered off with suction in between. The silica gel is finally dried at room temperature in vacuo at <0.005 atm.

TABLE II

| | Optically active polymers (V) on silica gel | | | | |
|---|---|---|---|---|---|
| Ex. No. | N-α-fluoroacryloylamino acid derivative according to Ex. | Preparation procedure | Yield (g) | [N-content] (%) | Silica gel-bound polymer content (% by weight) |
| 11 | 1 | 1b | 3.3 | 1.0 | 18.9 |
| 12 | 2 | 1c | 3.3 | 0.75 | 15.0 |
| 13 | 3 | 1b | 3.15 | 0.7 | 14.0 |
| 14 | 4 | 1b | 3.35 | 0.75 | 15.7 |
| 15 | 5 | 1b | 3.15 | 0.55 | 14.8 |
| 16 | 6 | 1b | 3.1 | 0.65 | 13.9 |
| 17 | 7 | 1b | 3.25 | 0.75 | 15.9 |
| 18 | 8 | 1b | 3.4 | 0.65 | 13.8 |
| 19 | 9 | 1b | 3.05 | 0.7 | 13.0 |
| 20 | 10 | 1b | 3.1 | 0.9 | 18.0 |

2. Preparation in the form of bead polymers

A solution of 13.5 g of optically active N-α-fluoroacryloylamino acid derivative, 1.5 g of ethylene glycol dimethacrylate and 0.3 g of azobisisobutyronitrile in 37.5 g of trichloromethane is dispersed in a solution of 3 g of polyvinyl alcohol in 130 ml of deionized water, with stirring. The apparatus is evacuated several times and filled with nitrogen. The polymerization mixture is stirred first at room temperature for 30 minutes under nitrogen and then at 55° C. (internal temperature) for 16 hours. The polymerization mixture is then stirred into 2 to 3 l of water, and the liquid phase is decanted, after the bead polymer has settled. The bead polymer is freed from the fines (polymer having a particle size of <10 μm) by suspending it in water and decanting the liquid phase 3 to 4 times, and, after thorough washing with acetone, dried to constant weight at 60° C.

In Table III below, the N-α-fluoroacryloylamino acid derivatives used for the polymerization, the stirring rate at which the polymerization was carried out, the yields in which the polymers were obtained, the particle size thereof and the volume of the bead polymers obtained in a dry ($V_{us}$) and swollen ($V_s$) state (swelling agent: toluene=T or toluene/THF 3:2 v/v mixture=T/T) are summarized.

TABLE III

Optically active polymers (V) as bead polymers

| Ex. No. | N-fluoroacryloylamino acid derivative according to Example | Stirring rate [rpm] | Yield of beads >10 μm (g) | Particle size of the beads (μm) | $V_{us}$ (ml/g) | $V_s$ (ml/g) | Swelling agent |
| --- | --- | --- | --- | --- | --- | --- | --- |
| 21 | 1 | 500 | 9.8 | 15–80 | 1.8 | 5.5 | T |
| 22 | 2 | 450 | 9.2 | 15–70 | 2.1 | 5.7 | T |
| 23 | 3 | 350 | 11.7 | 20–120 | 1.6 | 5.5 | T |
| 24 | 4 | 400 | 12.3 | 20–110 | 1.6 | 5.2 | T |
| 25 | 5 | 400 | 12.1 | 15–80 | 1.6 | 6.0 | T/T |
| 26 | 6 | 400 | 12.4 | 15–80 | 1.7 | 5.7 | T |
| 27 | 7 | 450 | 11.8 | 15–85 | 2.3 | 5.5 | T/T |
| 28 | 8 | 450 | 11.6 | 15–80 | 1.8 | 5.6 | T/T |
| 29 | 9 | 450 | 12.2 | 15–75 | 1.9 | 6.3 | T/T |
| 30 | 10 | 450 | 12.0 | 20–110 | 1.6 | 4.8 | T |

III.

Use of the N-α-fluoroacryloylamino acid derivatives (I) as adsorbents for the resolution of racemates The following test racemates were used for the chromatographic resolutions as shown in the drawings:
Racemate No. 1: Oxazepam
Racemate No. 2: Binaphthol
Racemate No. 3: Chlorothalidone
Racemate No. 4: Thalidomide
Racemate No. 5: N-3,5-dinitrobenzoylleucine
Racemate No. 6: 3-r-(benzenesulphonamido)-9-(2-carboxyethyl)-1,2,3,4,4a,9a-hexahydrocarbazole The silica gel-bound polymers were used in steel columns (inner diameter: 4 mm, length: 25 cm). n-Heptane/tetrahydrofuran 3:2 mixtures=eluent a, 1:1=eluent b, 1:2=eluent c, were used as eluents; the eluent rate was 1 ml/min.

The chromatograms shown below demonstrate the surprisingly good separation efficiency of the polymers according to the invention. The abscissa shows the elution time in minutes. Detection was carried out by UV absorption.

By comparison with the polymers according to the invention, it was sought to resolve the test racemates 2 and 4 in eluent a and the test racemate 3 in eluent b on a silica gel column covered with N-acryloylphenylalanine ethyl ester (Chirasphe ® from Merck). In all cases, upon UV detection, no enantiomer resolution was observed, and the enantioselectivity α was 1.00, although the polymer used differed from the polymer of Example 11 only through the missing fluorine substitution.

FIG. 1
Racemate No. 1
Adsorbent according to Example 17
Eluent: a

Figure 2:
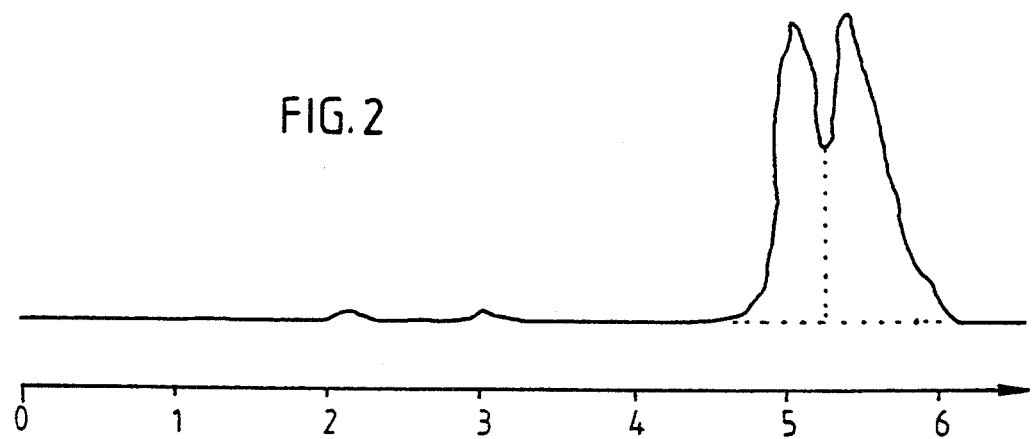

FIG. 2
Racemate No. 2
Adsorbent according to Example 11
Eluent: a

Figure 3:
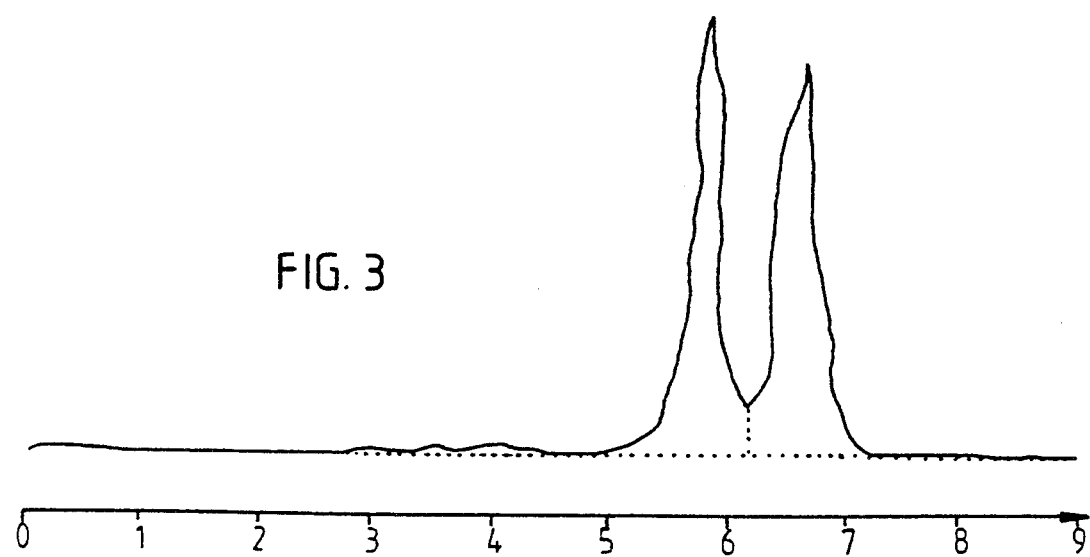

FIG. 3
Racemate No.2
Adsorbent according to Example 16
Eluent: a

Figure 4:
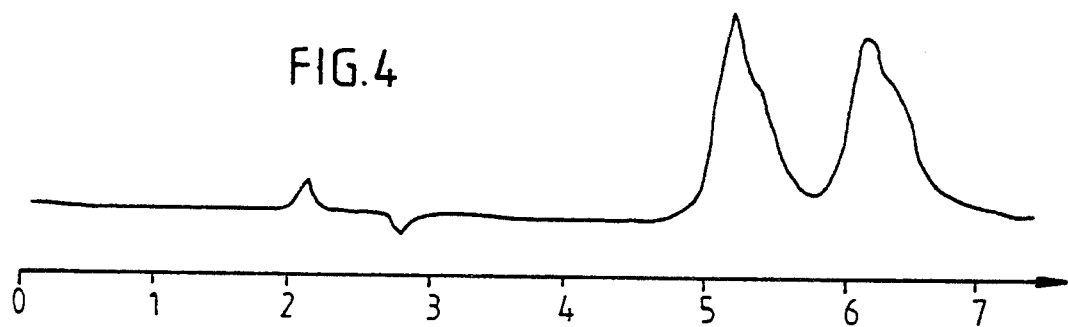

FIG. 4
Racemate No. 3
Adsorbent according to Example 11
Eluent: b

Figure 5:
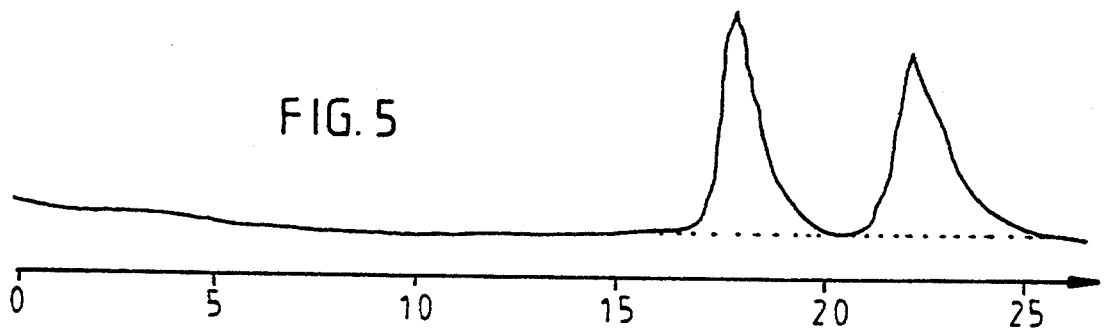

FIG. 5
Racemate No. 4
Adsorbent according to Example 11
Eluent: c

Figure 6:
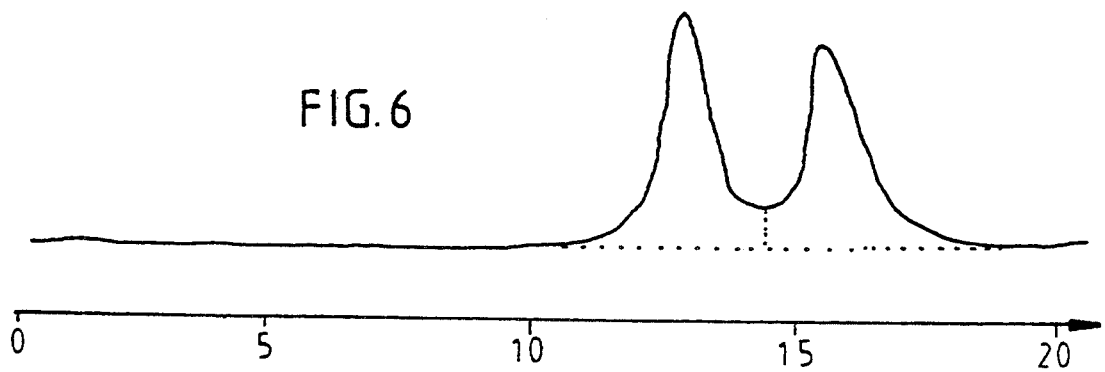

FIG. 6
Racemate No. 4
Adsorbent according to Example 18
Eluent: a

Figure 7:
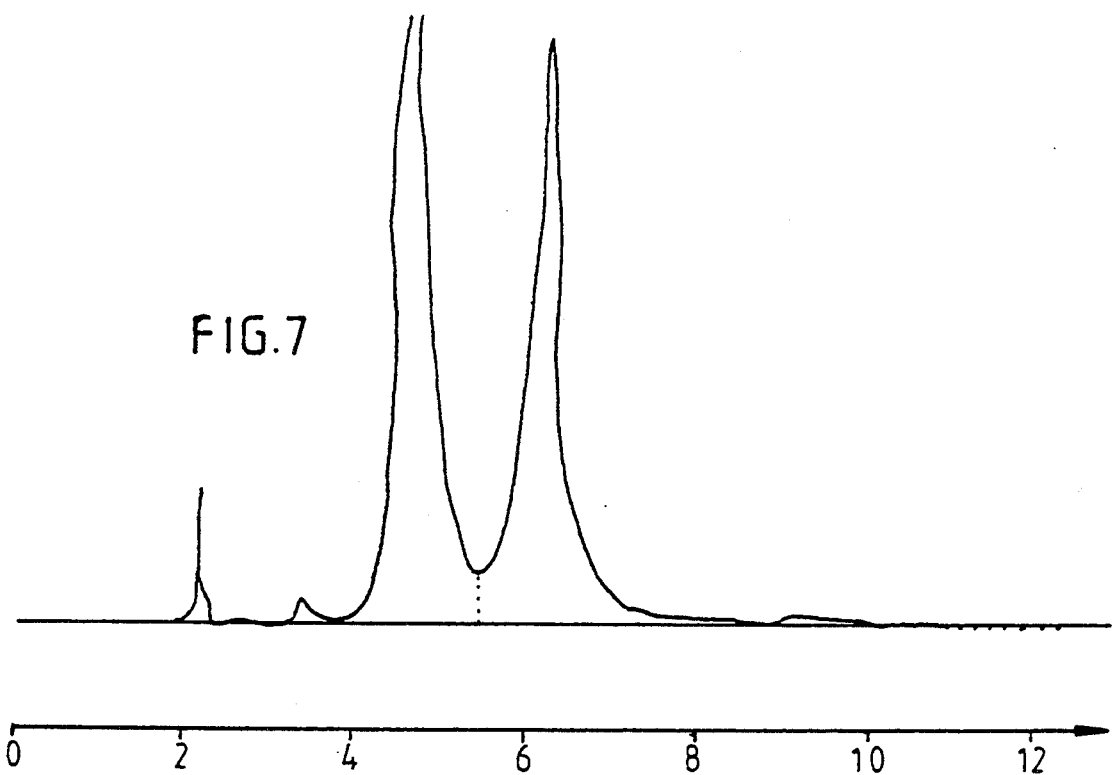

FIG. 7
Racemate No. 5
Adsorbent according to Example 17
Eluent: a

Figure 8:
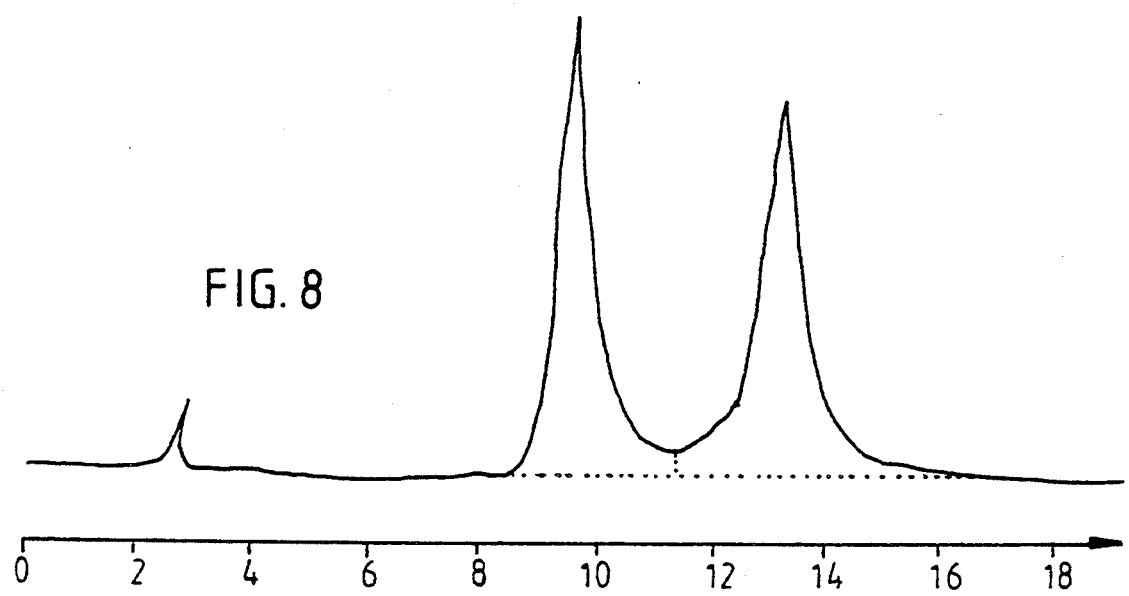

FIG. 8
Racemate No. 6
Adsorbent according to Example 16
Eluent: a

Figure 9:
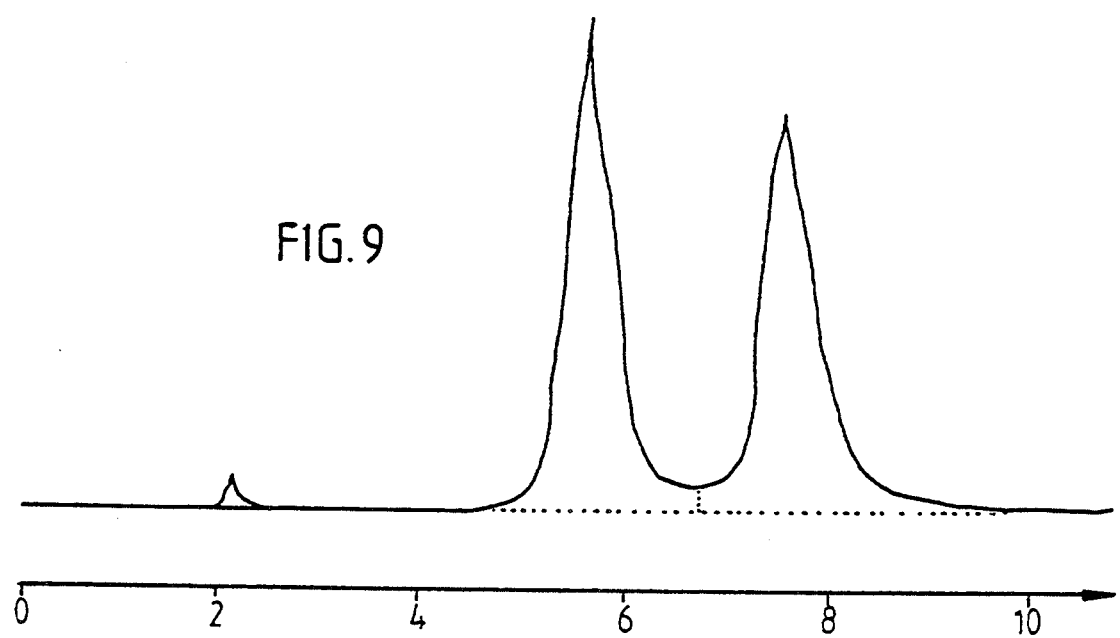

FIG. 9
Racemate No. 6
Adsorbent according to Example 18
Eluent: a

It will be understood that the specification and examples are illustrative but not limitative of the present invention and that other embodiments within the spirit and scope of the invention will suggest themselves to those skilled in the art.

We claim:
1. An N-α-fluoroacryloylamino acid derivative of the formula

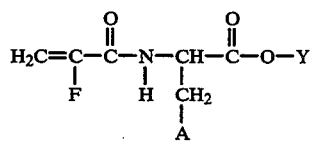

wherein

A is hydrogen or phenyl, and

Y is lower alkyl of 2 to 4 carbon atoms,

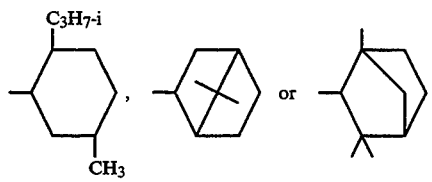

provided that when A is hydrogen Y is not lower alkyl of 2 to 4 carbon atoms.

2. A compound according to claim 1, wherein such compound is N-fluoroacryloyl-L-phenylalanine ethyl ester of the formula

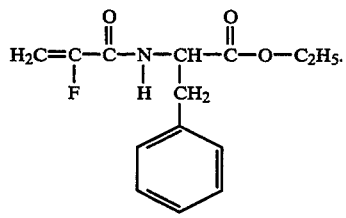

3. A compound according to claim 1, wherein such compound is N-fluoroacryloyl-L-alanine d-menthyl ester of the formula

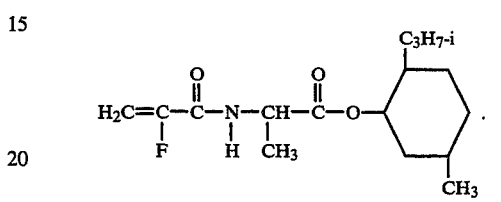

4. A compound according to claim 1, wherein such compound is N-fluoroacryloyl-L-alanine 1-bornyl ester of the formula

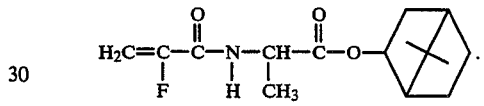

5. A compound according to claim 1, wherein such compound is N-fluoroacryloyl-L-alanine (+)-fenchyl ester of the formula

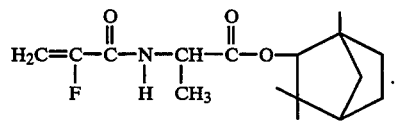

* * * * *